US011878189B2

(12) United States Patent
Givehchi et al.

(10) Patent No.: US 11,878,189 B2
(45) Date of Patent: *Jan. 23, 2024

(54) BEAM-OFF MOTION THRESHOLDS IN RADIATION THERAPY BASED ON BREATH-HOLD LEVEL DETERMINATION

(71) Applicant: SIEMENS HEALTHINEERS INTERNATIONAL AG, Palo Alto, CA (US)

(72) Inventors: Nasim Givehchi, Zürich (CH); Claas Wessels, Dübendorf (CH); Toon Roggen, Villigen (CH); Pascal Paysan, Basel (CH); Marius Heinrich Walter Koehl, Oberrohrdorf (CH); Stefan Georg Scheib, Waedenswil (CH)

(73) Assignee: SIEMENS HEALTHINEEERS INTERNATIONAL AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/900,861

(22) Filed: Aug. 31, 2022

(65) Prior Publication Data
US 2022/0409931 A1    Dec. 29, 2022

Related U.S. Application Data

(63) Continuation of application No. 17/138,856, filed on Dec. 30, 2020, now Pat. No. 11,433,257.

(51) Int. Cl.
*A61N 5/00*     (2006.01)
*A61N 5/10*     (2006.01)

(52) U.S. Cl.
CPC ......... *A61N 5/1068* (2013.01); *A61N 5/1049* (2013.01); *A61N 5/1067* (2013.01);
(Continued)

(58) Field of Classification Search
None
See application file for complete search history.

(56) References Cited

U.S. PATENT DOCUMENTS 10,500,418 B2   12/2019  Filiberti et al.
11,433,257 B2*   9/2022  Givehchi ............. A61N 5/1049
(Continued)

FOREIGN PATENT DOCUMENTS

GB     2583515 A    11/2020

OTHER PUBLICATIONS

Jung Ae Lee et al., "Four-Dimensional Computed Tomography Based Respiratory Gated Radiotherapy with Respiratory Guidance System: Analysis of Respiratory Signals and Dosimetric Comparison", Journal of Biomedicine and Biotechnology, Sep. 7, 2014, 10 pages, vol. 2014, Hindawi Publishing Corporation.

(Continued)

*Primary Examiner* — Hoon K Song
(74) *Attorney, Agent, or Firm* — SU IP CONSULTING

(57) ABSTRACT

A computer-implemented method of performing a treatment fraction of radiation therapy comprises: determining a current position of a target volume of patient anatomy; based on the current position of the target volume, computing an accumulated dose for non-target tissue proximate the target volume; determining that the accumulated dose is less than a current value for a dose budget of the non-target tissue; and in response to the accumulated dose being less than the current value for the dose budget, applying a treatment beam to the target volume while the target volume is in the current position.

20 Claims, 13 Drawing Sheets

(52) U.S. Cl.
CPC .... *A61N 5/1071* (2013.01); *A61N 2005/1061* (2013.01); *A61N 2005/1072* (2013.01)

(56) References Cited

U.S. PATENT DOCUMENTS

| | | |
|---|---|---|
| 2009/0161827 A1 | 6/2009 | Gertner et al. |
| 2010/0020931 A1 | 1/2010 | Otto et al. |
| 2010/0150309 A1* | 6/2010 | Nord .................... A61N 5/1071 378/65 |
| 2011/0222660 A1 | 9/2011 | Wang et al. |
| 2012/0184841 A1 | 7/2012 | Nielsen et al. |
| 2015/0306423 A1 | 10/2015 | Bharat et al. |
| 2019/0247676 A1 | 8/2019 | Peltola et al. |
| 2020/0030633 A1 | 1/2020 | Van Heteren et al. |
| 2022/0203134 A1 | 6/2022 | Givehchi et al. |

OTHER PUBLICATIONS

Stine Korreman, Ph.D. et al., "Respiration-Correlated Image Guidance Is the Most Important Radiotherapy Motion Management Strategy for Most Lung Cancer Patients", International Journal of Radiation Oncology, Biology & Physics, 2012, pp. 1338-1343, vol. 83, No. 4.

International Search Report and Written Opinion of the International Searching Authority, International application No. PCT/EP2021/086753, dated Apr. 19, 2022.

\* cited by examiner

BEAM-OFF MOTION THRESHOLDS IN RADIATION THERAPY BASED ON BREATH-HOLD LEVEL DETERMINATION

CROSS-REFERENCE TO RELATED APPLICATION

The present application is a continuation under 35 U.S.C. § 120 of U.S. Pat. No. 17,138,856, filed Dec. 30, 2020. The aforementioned U.S. patent application is incorporated herein by reference.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area. From such imaging, the size and mass of the target tissue can be estimated, a planning target volume determined, and an appropriate treatment plan generated.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues immediately before or while radiation treatment is delivered to the planning target volume. IGRT incorporates imaging coordinates from the treatment plan to ensure the patient is properly aligned for treatment in the radiation therapy device.

SUMMARY

In accordance with at least some embodiments of the present disclosure, a method of breath-hold-based radiation therapy is disclosed that employs beam-off thresholds for allowable movement of a target region (or volume) of patient anatomy relative to a planned treatment location for the target volume. The beam-off thresholds are based on one or more dosimetrically determined treatment breath-hold levels for a particular patient. In some embodiments, a treatment breath-hold level for the particular patient is determined based on imaging of the target volume at multiple breath-hold levels, a treatment plan for the treatment breath-hold level is generated, and the beam-off thresholds are determined based on dosing information that is calculated using image information for one or more breath-hold levels that are proximate to the treatment breath-hold level. In some embodiments, breath-hold level of the patient is monitored during treatment based on an external breathing signal (measured using a fiducial or other external marker, for example), X-ray imaging of the target volume, or a combination of both. Further, in some embodiments, dynamic beam-off thresholds are employed that are modified during a treatment fraction based on dose acquired in non-target tissue during the treatment fraction.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
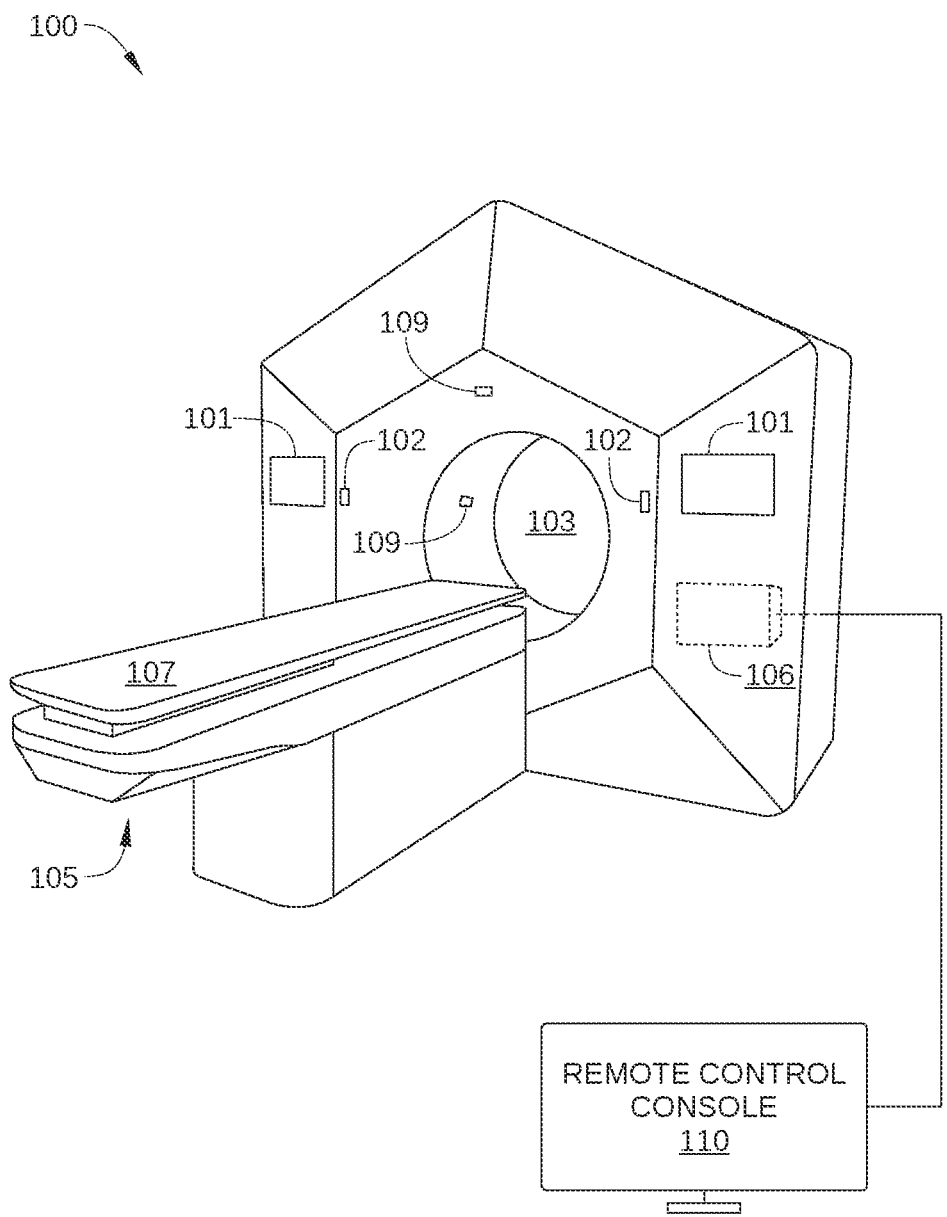
FIG. 1 is a perspective view of a radiation therapy system that can beneficially implement various aspects of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

Image guided radiation therapy (IGRT) is used to treat tumors in areas of the body that are subject to voluntary movement, such as the lungs, or involuntary movement, such as organs affected by peristalsis, gas motion, muscle contraction and the like. IGRT involves the use of an imaging system to view target tissues (also referred to as the "target volume") immediately before or while radiation treatment is delivered thereto. In IGRT, image-based coordinates of the target volume from a previously determined treatment plan are compared to image-based coordinates of the target volume determined immediately before or during the application of the treatment beam. In this way, changes in the surrounding organs at risk and/or motion or deformation of the target volume relative to the radiation therapy system can be detected. Consequently, dose limits to organs at risk are accurately enforced based on the daily position and shape, and the patient's position and/or the treatment beam can be adjusted to more precisely target the radiation dose to the tumor. For example, in pancreatic tumor treatments, organs at risk include the duodenum and stomach. The shape and relative position of these organs at risk with respect to the target volume can vary significantly from day-to-day. Thus, accurate adaption to the shape and relative position of such organs at risk enables escalation of the dose to the target volume and better therapeutic results.

In some radiation therapy systems, breath-hold-based radiation therapy is performed, in which the patient performs one or more breath holds throughout the treatment fraction. Breath-hold-based radiation therapy is often employed to separate an organ at risk or other critical anatomical structure from the target volume during the beam delivery of the treatment fraction. In addition, breath-hold-based radiation therapy can reduce the motion and/or deformation of a target volume caused by patient respiration, thereby reducing the dose received by non-target tissue. However, maintaining a breath hold for the time intervals associated with radiation therapy can be challenging for many patients, and significant motion of a target volume can occur due to involuntary loss of the breath hold during breath-hold-based radiation treatment. Further, no patient can maintain a perfectly motionless breath hold and, as a result, at least some motion of a target volume typically occurs throughout a breath hold.

In conventional radiation therapy systems, when the detected motion of a target volume exceeds a predetermined motion threshold during treatment, the treatment beam is typically shut off (gated) to prevent violation of the dosimetric constraints for non-target tissue. As a result, the duration of the breath-hold-based portion of a treatment fraction is extended, which can be uncomfortable for a patient, or even exceed the ability of the patient to remain motionless. Accordingly, there is a need in the art for improved systems and techniques for beam-off motion thresholds in radiation therapy.

According to various embodiments, beam-off motion thresholds are based on one or more dosimetrically determined treatment breath-hold levels for a particular patient. Beam-off motion thresholds determined as described herein are a better indicator of the dosimetric consequences of patient motion that is detected during radiation treatment than conventional beam-off motion thresholds, which are based on external measurements not precisely representing the motion of internal anatomical structures. Therefore, the herein-described beam-off motion thresholds for a target region can provide sufficient margin around a planned treatment location for the target region to limit significant misalignment between treatment fields and non-target tissue without imposing overly strict beam-off conditions that result in frequent beam holds during radiation treatment. Thus, the trade-off between dose delivered to the target volume and dose received by critical anatomical structures is minimized or otherwise reduced. Further, in some embodiments, dynamic beam-off thresholds are employed that are modified during a portion of a treatment fraction based on dose acquired in non-target tissue during that portion of the treatment fraction. For example, in such embodiments, as a dose budget for non-target tissue is expended during a breath-hold-based portion of a treatment fraction, a beam-off motion threshold is reduced, so that later in the same breath-hold-based portion of the treatment fraction, less motion of the target volume relative to the planned treatment location may cause a beam hold to occur. In such embodiments, motion of the target volume away from the planned treatment location generally does not result in a beam hold until a dose budget for the non-target tissue is exceeded. As a result, a brief excursion of the target volume away from the planned treatment location usually does not result in a beam hold, and the duration of that breath-hold-based portion of the treatment fraction is not increased.

FIG. 1 is a perspective view of a radiation therapy system 100 that can beneficially implement various aspects of the present disclosure. Radiation therapy (RT) system 100 is a radiation system configured to detect intra-fraction motion in near-real time using X-ray imaging techniques. Thus, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, radiation therapy system 100 is described herein configured with a circular gantry. In other embodiments, radiation therapy system 100 can be configured with a C-gantry capable of infinite rotation via a slip ring connection or a C-arm configured with cable wind-up. Further, in some embodiments, RT system 100 is configured to generate a treatment beam of proton and/or other heavy charged particles in addition to or in lieu of an X-ray treatment beam. In some embodiments RT system 100 may be any external beam radiation delivery system known in the art or available on the market.

Generally, RT system 100 is capable of kV imaging of a target volume immediately prior to or during application of an MV treatment beam, so that an IGRT and/or an intensity-modulated radiation therapy (IMRT) process can be performed using X-ray imaging. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location.

In some embodiments, RT system 100 further includes one or more patient-monitoring optical sensors 109 disposed proximate couch 107. In some embodiments, one or more of optical sensors 109 are mounted on an end of couch 107 opposite bore 103. Alternatively or additionally, patient-monitoring optical sensors 109 may be disposed proximate bore 103 and/or in a treatment room containing RT system 100. Patient-monitoring optical sensors 109 are configured as a patient position-monitoring system that generates an external motion signal indicating a specific magnitude of respiratory motion by a patient on couch 107. Thus, patient-monitoring optical sensors 109 can obtain a motion trace of one or more points on a surface of the body of the patients, for example based on the motion of a fiducial or other external marker (or markers) that is/are positioned to move synchronously with a target volume of the patient. In another example, in some embodiments, patient-monitoring optical sensors 109 are configured to monitor respiratory motion via surface measurement based on optical processing of a markerless surface of the body of the patient. In some embodiments, a motion trace obtained by patient-monitoring sensors 109 can be correlated to specific internal motion of anatomical structures of the patient that is detected via X-ray imaging, magnetic resonance imaging (MRI), and/or the like. In some embodiments, patient-monitoring optical sensors 109 include one or more cameras, surface scanners, and the like.

Figure 2:
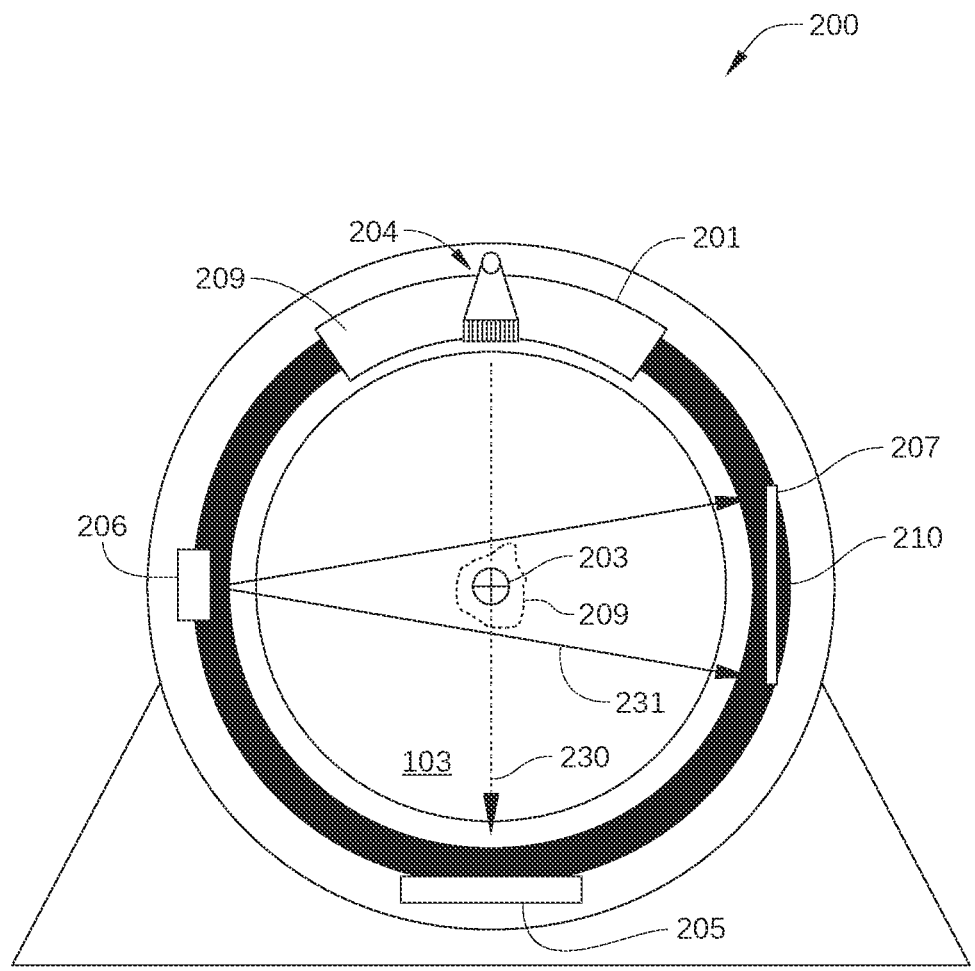
FIG. 2 schematically illustrates a drive stand and gantry of the radiation therapy system of FIG. 1, according to various embodiments.

FIG. 2 schematically illustrates a drive stand 200 and gantry 210 of RT system 100, according to various embodiments. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 220 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons, protons, and/or other heavy charged particles, ultra-high dose rate X-rays (e.g., for FLASH radiotherapy) or microbeams for microbeam radiation therapy) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration. The embodiment of drive system 201 depicted in FIG. 2 is provided as an example configuration. In other embodiments, such as embodiments in which MV treatment beam 230 includes heavy charged particles and/or ultra-high dose rate X-rays, drive system 201 may have a substantially different configuration than that shown in FIG. 2.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In some embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can be generated. CBCT is often employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape. Alternatively, or additionally, in some embodiments, partial-data reconstruction is performed by RT system 100 during portions of an IGRT or IMRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. One such embodiment is illustrated in FIG. 3.

Figure 3:
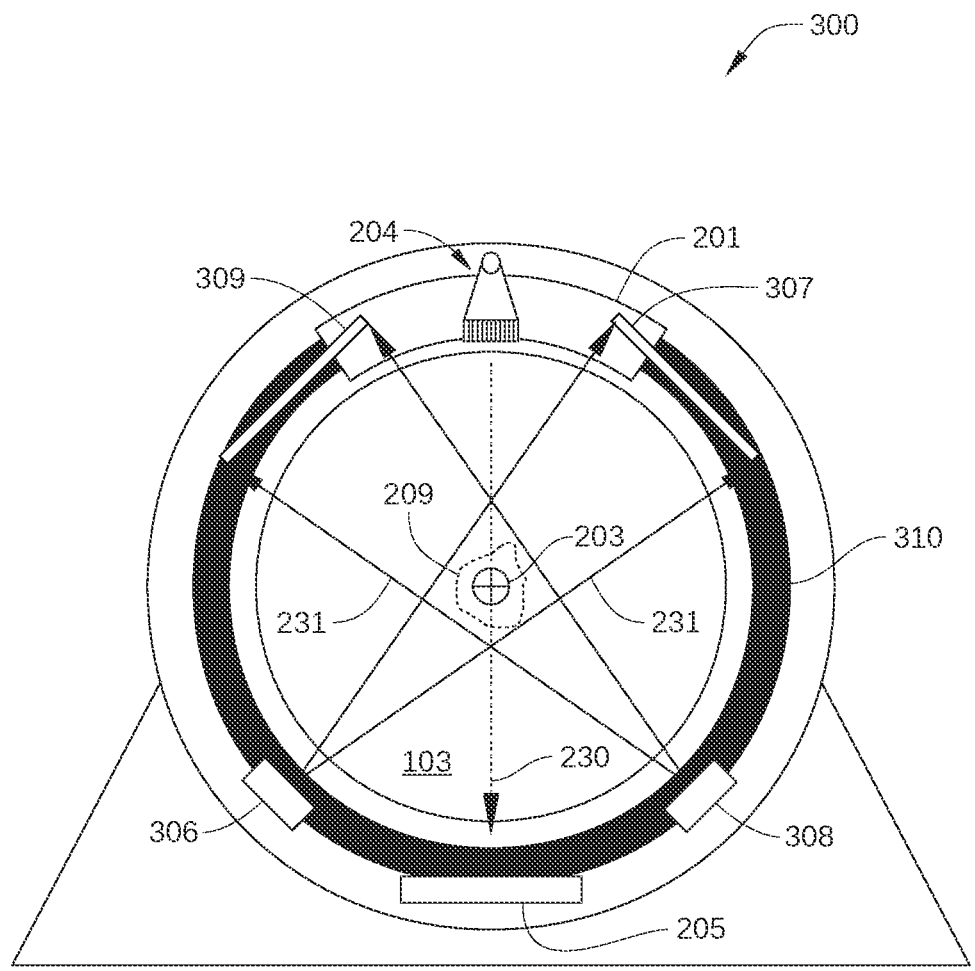
FIG. 3 schematically illustrates a drive stand and a gantry of the radiation therapy system of FIG. 1, according to various embodiments.

FIG. 3 schematically illustrates a drive stand 300 and gantry 310 of RT system 100, according to various embodiments. Drive stand 300 and gantry 310 are substantially similar in configuration to drive stand 200 and gantry 200 in FIG. 2, except that the components of RT system 100 that are mounted on gantry 310 include a first imaging X-ray source 306, a first X-ray imager 307, a second imaging X-ray source 308, and a second X-ray imager 309. In such embodiments, the inclusion of multiple X-ray imagers in RT system 100 facilitates the generation of projection images (for reconstructing the target volume) over a shorter image acquisition arc. For instance, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 207 (or by first x-ray imager 307 and second X-ray imager 309) are used to construct imaging data for a digital volume of patient anatomy within a 3D region that includes the target volume. Alternatively or additionally, such projection images can be used to update portions of an existing imaging data for the digital volume corresponding to the 3D region. One embodiment of such a digital volume is described below in conjunction with FIG. 4.

Figure 4:
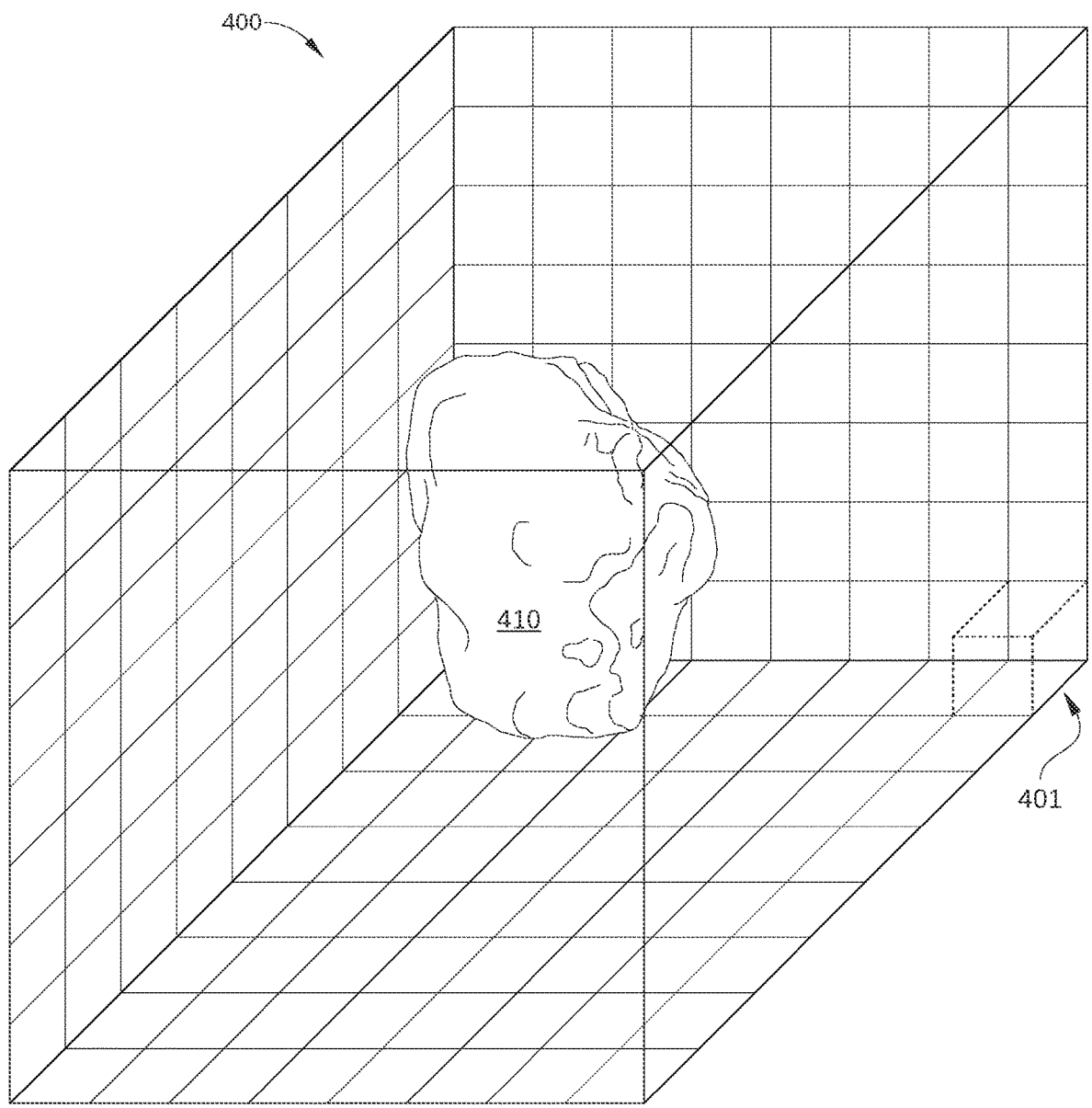
FIG. 4 schematically illustrates a digital volume that is constructed based on projection images generated by one or more X-ray images included in the radiation therapy system of FIG. 1, according to various embodiments.

FIG. 4 schematically illustrates a digital volume 400 that is constructed based on projection images generated by one or more X-ray imagers included in RT system 100, according to various embodiments. For example, in some embodiments, the projection images can be generated by a single X-ray imager, such as X-ray imager 207, and in other embodiments the projection images can be generated by multiple X-ray imagers, such as first x-ray imager 307 and second X-ray imager 309.

Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for sub-clinical disease spread, which is generally not imagable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 400.

According to various embodiments described below, image information associated with each voxel 401 of digital volume 400 is constructed via projection images generated by the single or multiple X-ray imagers via a CBCT process. For example, such a CBCT process can be employed immediately prior to delivering treatment beam 230 to target volume 410, so that the location and shape of target volume 410 can be confirmed before treatment begins. In addition, according to various embodiments described below, image information associated with some or all of voxels 401 of digital volume 400 is updated via projection images generated by the single or multiple X-ray imagers via a DTS process. For example, such a DTS process can be employed after a portion of a planned treatment has begun and before the planned treatment has completed. In this way, the location and shape of target volume 410 can be confirmed while the treatment is underway. Thus, if a sufficient portion of the target volume 410 is detected to be extending outside a threshold region, the treatment can either be aborted or modified. In such an instance, modification of the treatment can be accomplished by adjusting patient position and/or the treatment beam.

According to various embodiments, a radiation therapy process includes determining a specific breath-hold level (referred to herein as a "treatment breath-hold level") and employing the treatment breath-hold level during radiation therapy. The treatment breath-hold level is determined based on one or more dosimetric plan properties of a treatment plan, such as target coverage, organ-at risk (OAR) dose volume parameters, geometric parameters, and the like. The radiation therapy process further includes determining and employing beam-off thresholds for allowable movement of a target volume during the radiation therapy. The beam-off thresholds are based on a dosimetric analysis of the treatment breath-hold level and one or more breath-hold levels that are adjacent or proximate to the treatment breath-hold level. One such embodiment is described below in conjunction with FIG. 5.

Figure 5:
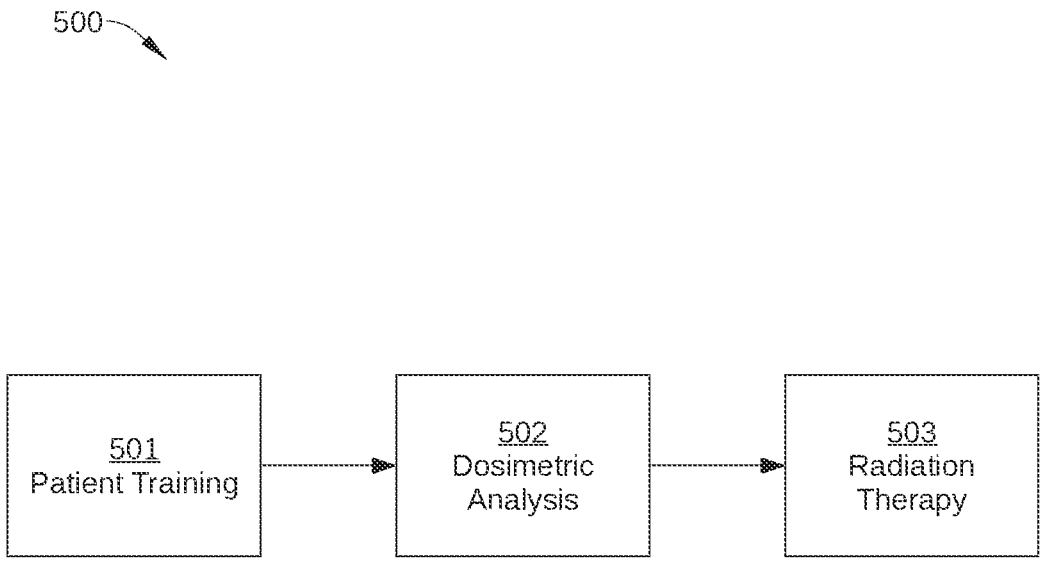
FIG. 5 is a block diagram illustrating a breath-hold-based radiation therapy process, according to various embodiments.

FIG. 5 is a block diagram illustrating a breath-hold-based radiation therapy process 500, according to various embodiments. In the embodiment illustrated in FIG. 5, breath-hold-based radiation therapy process 500 includes a patient training phase 501, a dosimetric analysis phase 502, and a radiation therapy phase 503.

In patient training phase 501, suitability of a particular patient for treatment via breath-hold-based radiation therapy process 500 is determined and the patient is educated and trained for the breath-hold procedures to be employed in dosimetric analysis phase 502 and radiation therapy phase 503. For example, in some embodiments, the capability of the patient is evaluated in a pre-image acquisition session for performing a breath hold at a level and for a duration that is compatible with the breath-hold based treatment included in breath-hold-based radiation therapy process 500. In the embodiments, the patient is trained to perform various breath-hold levels, where each breath-hold level corresponds to a unique volume of breath being held. It is noted that, for each breath-hold level, there is an associated configuration of the anatomical positions of internal structures. As part of the training process, the patient performs various breath-hold lengths and breath-hold repetitions to confirm that the patient can comply with the boundary conditions of the breath-hold based treatment included in breath-hold-based radiation therapy process 500. Successful completion of patient training phase 501 ensures that the patient is capable of undergoing CT image acquisition and the various breath-hold levels that occur in dosimetric analysis phase 502 and radiation therapy phase 503.

In some embodiments, in addition to static breath-hold training, a patient is trained in regular free-breathing that encompasses certain targeted breath-hold levels in patient training phase 501. Such supplemental training enables free-breathing-based approaches that can be employed as part of dosimetric analysis phase 502.

Various conventional techniques can be employed in patient training phase 501 to facilitate the breath-hold procedures of patient training phase 501. In some embodiments, audio-visual breath-hold guidance can be employed in patient training phase 501. Alternatively or additionally, intercostal muscle training and/or other breathing training can be employed in patient training phase 501 to improve breath-hold length or to guide breath-hold level and length. Alternatively or additionally, a mechanical ventilator can be employed in patient training phase 501 to improve breath-hold length or to guide breath-hold level and length.

In dosimetric analysis phase 502, a treatment breath-hold level for the patient is determined that causes a beneficial anatomical configuration of patient internal structures for radiation therapy. For example, a breath-hold level that is demonstrated to position a target volume away from a critical anatomical structure (such as an OAR) is a breath-hold level that may be selected as the treatment breath-hold level for the patient. In addition, beam-off motion thresholds are also determined in dosimetric analysis phase 502. Such beam-off motion thresholds indicate allowable movement of a target volume during radiation therapy phase 503. One embodiment of dosimetric analysis phase 502 is described below in conjunction with FIG. 6.

In radiation therapy phase 503, a treatment plan is implemented on the patient using the treatment threshold level and the beam-off motion thresholds determined in dosimetric analysis phase 502. Generally, radiation therapy phase 503 includes multiple treatment fractions, each of which may include a single or multiple breath-hold-based portions that each occur over a single breath hold. In some embodiments, radiation therapy phase 503 may include a single treatment fraction. Radiation therapy phase 503 is described below in conjunction with FIG. 11.

Figure 6:
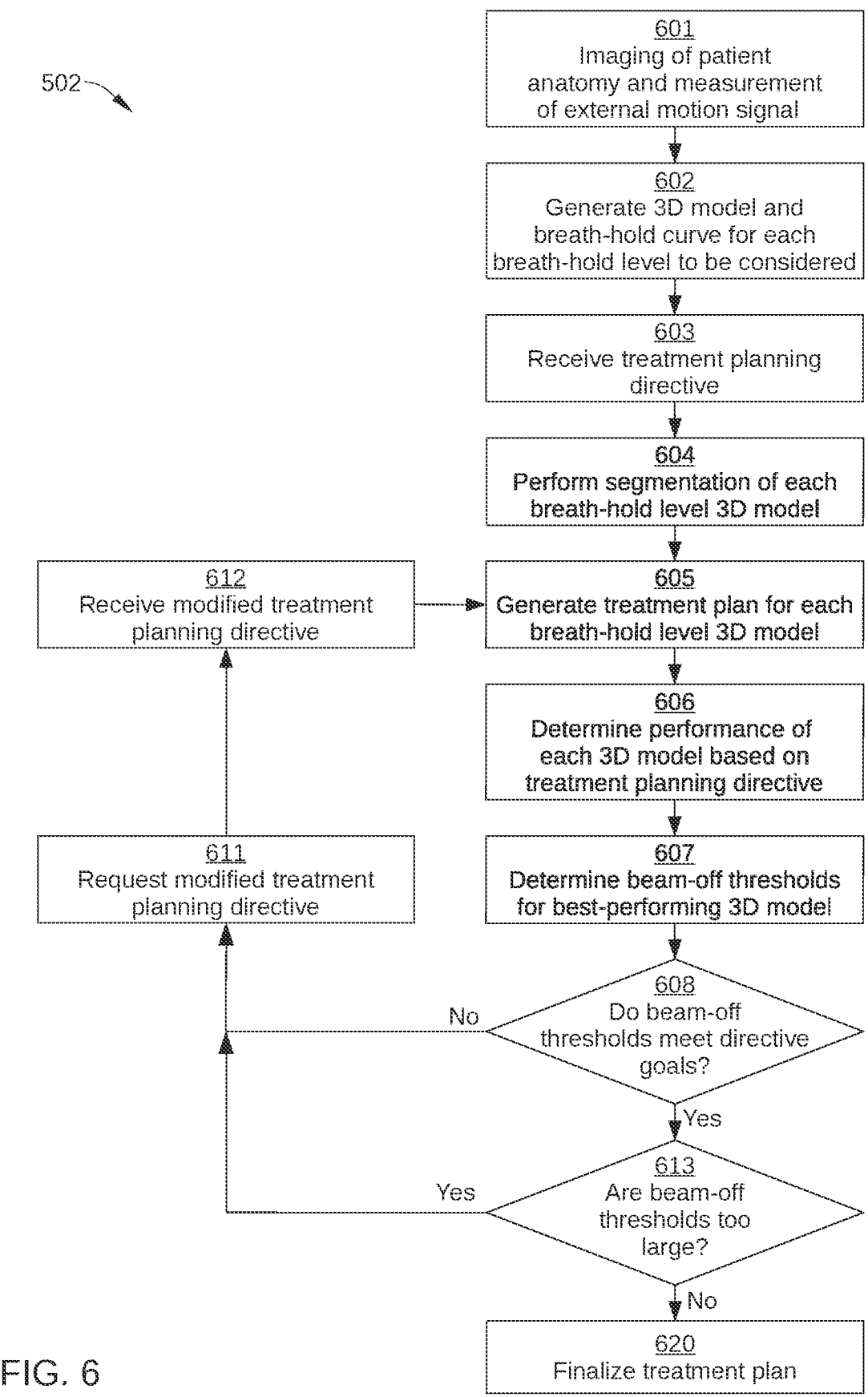
FIG. 6 sets forth a flowchart of the dosimetric analysis phase of FIG. 5, according to one or more embodiments.

FIG. 6 sets forth a flowchart of dosimetric analysis phase 502, according to one or more embodiments. As noted above, dosimetric analysis phase 502 includes a process for determining a treatment breath-hold level for a patient and for generating beam-off thresholds for allowable movement of a target volume during breath-hold-based radiation treatment of the patient. Dosimetric analysis phase 502 may include one or more operations, functions, or actions as illustrated by one or more of blocks 601-620. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although dosimetric analysis phase 502 is described in conjunction with the systems of FIGS. 1-4, persons skilled in the art will understand that any suitably configured radiation therapy system is within the scope of the present embodiments.

In step 601, a computing device causes imaging of the anatomy of a patient to be performed, such as treatment control computer 106 and/or remote control console 110 of FIG. 1, or any other suitable computing device. Specifically, for various breath-hold levels, a three-dimensional (3D) image is acquired and a corresponding breath-hold curve or other external motion signal is measured. Based on the 3D images and the breath-hold curves, a correlation between an external motion signal and a current position of a target volume and/or other internal anatomy can be established. Thus, during radiation treatment, measurement of the external motion signal can indicate the current position of the target volume without the use of X-ray or MRI imaging. In an alternative embodiment, no breath-hold curve is measured in step 601, and 3D imaging during treatment is employed to determine the current position of a target volume during the treatment.

In some embodiments, the 3D imaging performed in step 601 includes MRI imaging of an anatomical region surrounding a target volume. Alternatively or additionally, in some embodiments, the 3D imaging performed in step 601 includes X-ray imaging of the anatomical region, such as CBCT imaging and/or 4D-CT imaging. In 4D-CT, multiple phases (e.g., five to ten) of motion in the anatomical region is imaged. In such embodiments, the 4D-CT imaging may be performed in conjunction with trained and/or assisted free-breathing by the patient. In some embodiments, during the 3D imaging, audio-visual breath-hold guidance, a mechanical ventilator, and/or any other suitable technique can be employed to improve breath-hold length or to guide breath-hold level and length.

In some embodiments, the measurement of the external motion signal performed in step 601 includes obtaining a motion trace of a point or points on the surface of the body of the patient. For example, in some embodiments, the measurement of the external motion signal is performed via patient-monitoring optical sensors 109 and one or more fiducials, other markers, and/or position sensor(s). Thus, in such embodiments, motion associated with the respiration cycle of the patient is measured in conjunction with the above-described 3D imaging of the anatomical region surrounding the target volume. Generally, the location or locations of the fiducials, markers, and/or position sensors are selected so that said fiducials, markers, and/or position sensors move synchronously, or substantially synchronously, with the target volume of the patient.

In step 602, for each breath-hold level to be considered during dosimetric analysis phase 502, the computing device: generates a 3D model of the patient anatomy surrounding the target volume; determines a value for target position that indicates motion of the target volume at the breath-hold level; determines a specific value of the external motion signal that is associated with the breath-hold level; and correlates the specific value of the external motion signal with the value for target position. As a result of the correlation, target position can be inferred during a radiation treatment based on a measurement of the external motion signal.

Generally, the computing device generates each 3D model of the patient anatomy in step 602 based on a CT data set or MRI data set generated in step 601. In addition, in step 602 the computing device determines the value for target position for a breath-hold level via the 3D model for that breath-hold level. The target position value may indicate a position of a target volume, a position of a specific portion of a target volume (e.g., an edge region of the target volume or a center point of the target volume), a position of an OAR, a position of a specific portion of the OAR (e.g., an edge region of the OAR or a center point of an OAR), and the like. Such positions may be measured relative to any suitable datum location within or proximate to the anatomy of the patient. Further, in step 602 the computing device determines the specific value of the external motion signal for each breath-hold level via a different breath-hold curve, where each different breath-hold curve indicates the external motion signal for a particular breath hold. One embodiment of a breath-hold curve is described below in conjunction with FIG. 7.

Figure 7:
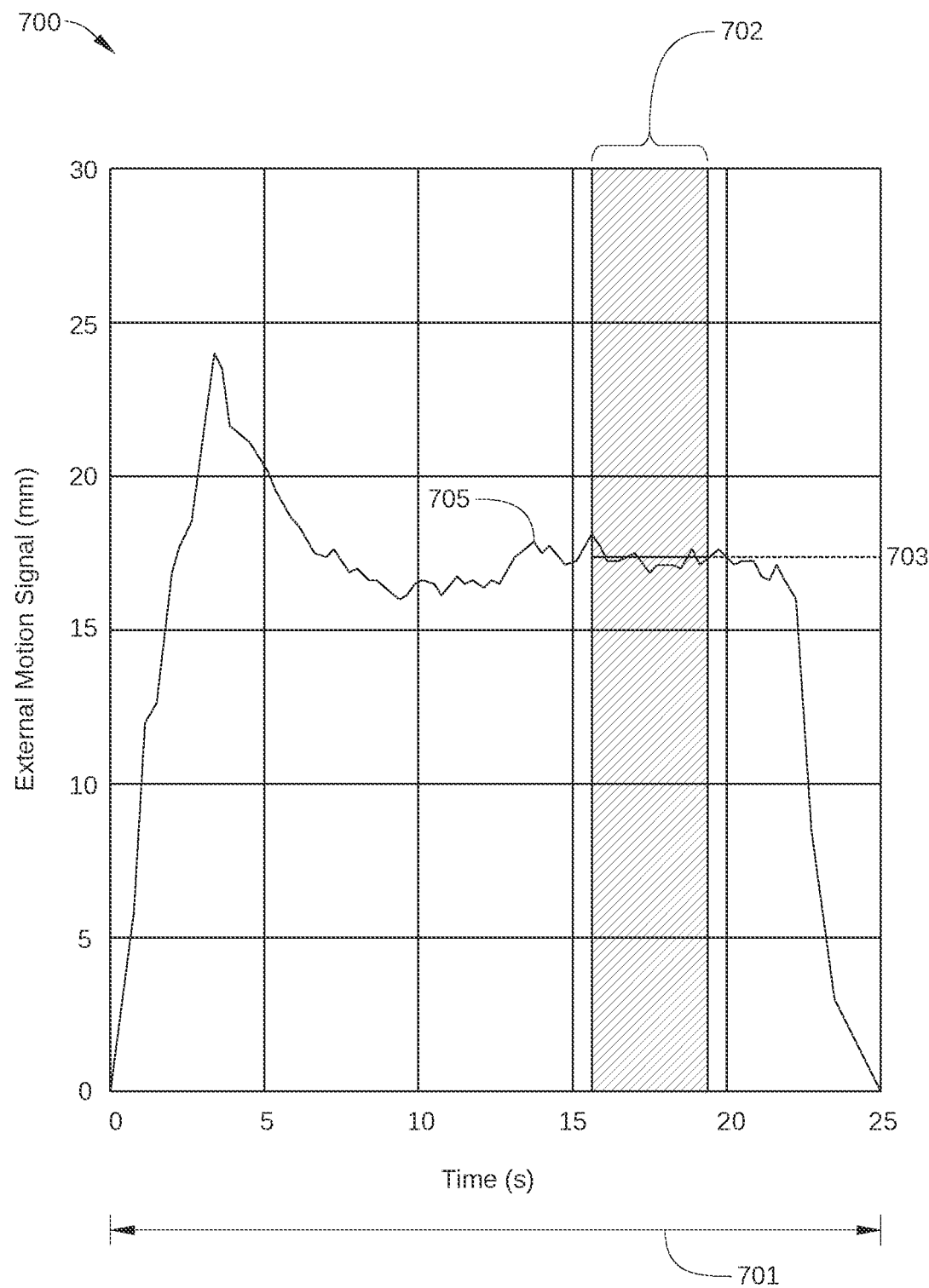
FIG. 7 is an illustration of a breath-hold curve, according to various embodiments.

FIG. 7 is an illustration of a breath-hold curve 700, according to various embodiments. Breath-hold curve 700 shows variations in external motion signal 705 over a time interval 701 that includes a patient breath hold, such as a patient breath hold performed during patient training phase 501, step 601 of dosimetric analysis phase 502, or radiation therapy phase 503. As described above, external motion signal 705 indicates a position of a point or points on the surface of the body of the patient, such as one or more fiducials, other markers, and/or position sensor(s). Such positions may be measured relative to any suitable datum location within or proximate to the anatomy of the patient.

As shown, the exact value of external motion signal 705 generally varies over time, even when the patient successfully maintains a breath hold throughout time interval 701. Also shown in FIG. 7 is an imaging interval 702 (cross-hatched), during which the 3D imaging of step 601 takes place. In some embodiments, the specific value of the external motion signal that is associated with breath-hold curve 700 is determined based at least in part on the 3D imaging of step 601. In such embodiments, the specific value of the external motion signal that is associated with breath-hold curve 700 may be based on some or all of the portion of breath-hold curve 700 that is disposed within imaging interval 702. For example, in one such embodiment, the specific value of the external motion signal associated with breath-hold curve 700 is based on an average value 703 of external motion signal 705 disposed within imaging interval 702. Thus, in such embodiments, the specific value of the external motion signal associated with breath-hold curve 700 (e.g., average value 703) can be correlated, via the above-described 3D imaging, to a specific configuration of the anatomical region surrounding the target volume that is imaged during imaging interval 702. As a result, an external motion signal measured during subsequent radiation therapy indicates target motion, as described below in conjunction with FIG. 8.

Figure 8:
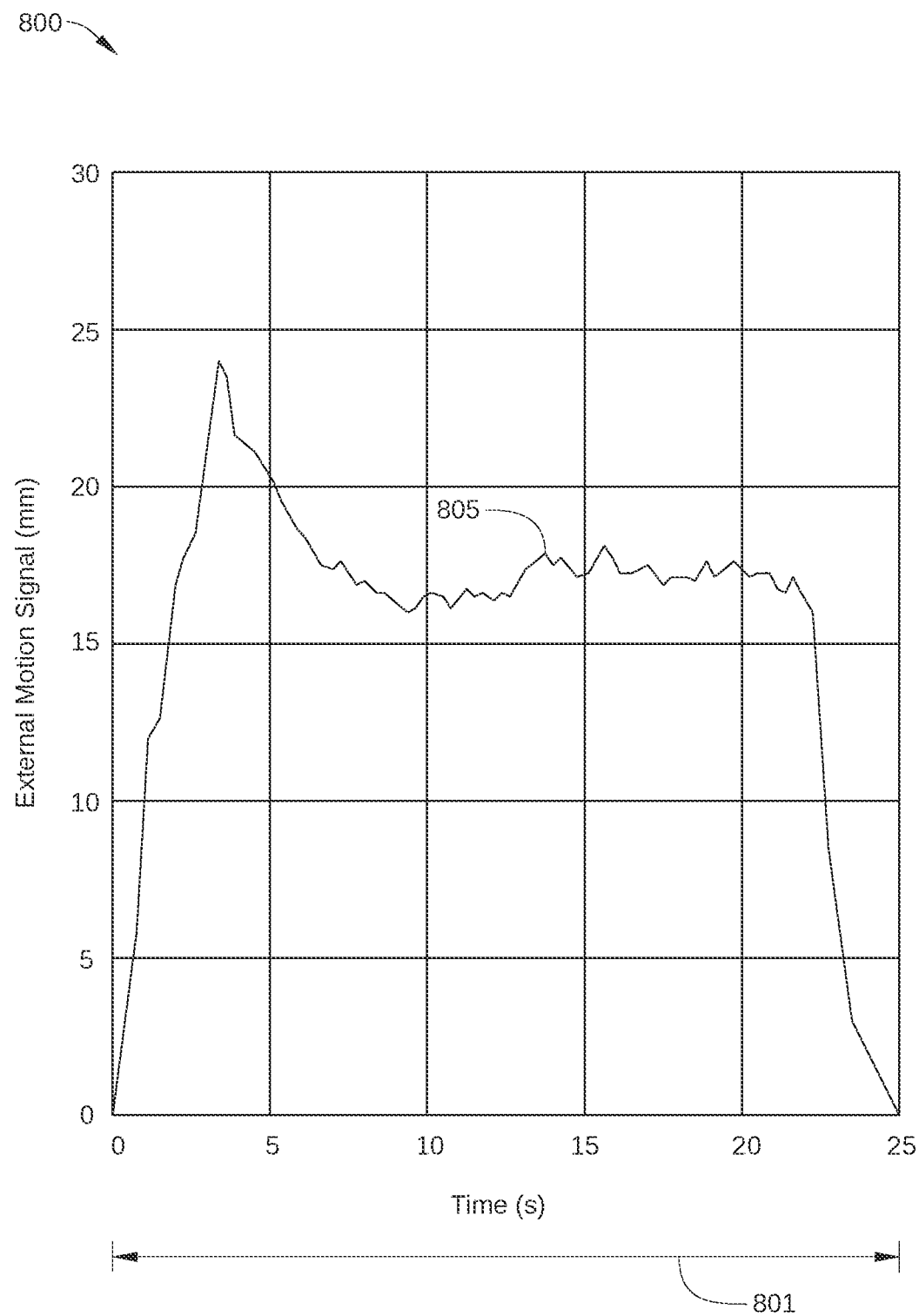
FIG. 8 is an illustration of a breath-hold correlation curve, according to various embodiments.

FIG. 8 is an illustration of a breath-hold correlation curve 800, according to various embodiments. Breath-hold correlation curve 800 shows variations in target position 805 over a time interval 801 that includes a patient breath hold, such as a patient breath hold performed during radiation therapy phase 503. Target position 805 indicates a position of a target associated with a target volume or OAR. In some embodiments, target position 805 is not measured directly, and instead is determined by a computing device based on an external motion signal that is correlated to target position 805. Alternatively, in some embodiments, target position 805 is based at least in part on 3D imaging of the anatomical region surrounding the target volume, other 2D X-ray imaging, and/or digital tomosynthesis (DTS) imaging. In such embodiments, information included in such imaging can be employed to correct target position 805 during radiation therapy phase 503 for more accurate calculation of dose received by non-target tissue. In either case, breath-hold correlation curve 800 can be employed in conjunction with beam-off thresholds during radiation therapy phase 503, as described below, to reduce dose received by non-target tissue without imposing overly strict beam-off conditions that result in frequent beam holds during radiation treatment.

Returning to FIG. 6, in some embodiments, one or more interpolated breath-hold levels and associated 3D models are also generated in step 602. For example, in an instance in which five 3D CT scans are performed for five different breath-hold levels (e.g., breath-hold levels 1-5), one or more additional breath-hold levels are generated between breath-hold levels 1 and 2 based on interpolation between the breath-hold levels 1 and 2, and one or more additional 3D models are generated based on the 3D models associated with breath-hold levels 1 and 2. Similarly, one or more additional breath-hold levels and 3D models can be generated between breath-hold levels 2 and 3 and between breath-hold levels 3 and 4. In such embodiments, interpolation between 3D models can be performed based on deformable image registration of acquired 3D information, such as acquired CT data.

In step 603, a treatment planning directive is received, for example from a physician, such as a radiation oncologist, or from treatment planning software. The physician intent of the treatment is specified in the treatment planning directive, and may include pre-defined dose volume and/or geometric parameters, such as a minimum distance of dose-limiting OARs and/or margins to be applied to such OARs.

The treatment planning directive may be generated based on some or all of the 3D models generated in step 602. The treatment planning directive typically describes image studies for a treatment site, including target tissue structures and normal tissue structures to be defined via the imaging studies. These target and normal tissue structures are subsequently used for treatment planning. For scoring multiple treatment plans within an optimization process, the treatment planning directive may also specify expansions of the target tissue structures and normal tissue structures. Thus, in addition to the gross tumor volume (GTV), the treatment planning directive may further include clinical target volume (CTV), the internal target volume (ITV), the planning target volume (PTV), OARs, and/or a planning organ at risk volume (PRV), among others. The treatment planning directive may further specify radiation therapy prescription guidelines, planning suggestions, and/or special instructions.

In some instances, a radiation oncologist generates some or all of the treatment planning directive, for example based on local clinical standards, specific medical conditions of the patient, and the like. Alternatively, in some instances, the radiation oncologist can be assisted by a software application configured to suggest some or all of the information included in the treatment planning directive.

In step 604, the computing device performs segmentation of each breath-hold level 3D model generated in step 602. For example, in some embodiments, for each 3D model, an auto segmentation of the OAR and target volume is performed. Alternatively, in some embodiments, the segmentation for one or more of the 3D models is performed manually by a physician.

In step 605, the computing device generates a treatment plan for each breath-hold level 3D model generated in step 602. Generally each such treatment plan is generated based at least in part on the physician intent specified in the treatment planning directive. Each treatment plan may include one or more beam geometries, a dose distribution for each beam geometry, and the treatment fractions for implementing the planned treatment.

In step 606, the computing device determines performance of each 3D model and associated treatment plan. For example, in some embodiments, the computing device performs a dosing simulation for each 3D model and associated treatment plan and compares the simulated dosing to the dose volume and/or geometric parameters specified in the treatment planning directive. In some embodiments, the dosing simulation for each 3D model and associated treatment plan is performed assuming that no motion of the target volume occurs. In such embodiments, only non-motion margins are applied to the target volume.

In step 607, the computing device determines beam-off thresholds for the best-performing 3D model and associated treatment plan scored in step 606. The beam-off thresholds indicate allowable movement of a target volume during breath-hold-based radiation treatment of the patient when the patient performs a breath-hold at the breath-hold level that corresponds to the best-performing 3D model (referred to herein as the "treatment breath-hold level").

In some embodiments, the beam-off thresholds are determined in step 607 by applying the treatment plan associated with the best-performing 3D model to the one or more neighboring breath-hold levels. In this way, the dosing of non-target tissue that occurs during a treatment fraction when a patient involuntarily varies breath-hold level from the treatment breath-hold level to a neighboring breath-hold level can be estimated. In the embodiments, each beam-off threshold corresponds to a breath-hold level that is different from the treatment breath-hold level but still does not result in violation of one or more dosing parameters specified in the treatment planning directive.

In some embodiments, the computing device determines static beam-off thresholds for the treatment plan, and in other embodiments, the computing device determines dynamic beam-off thresholds for the treatment plan. An embodiment of static beam-off thresholds is described below in conjunction with FIG. 9, and an embodiment of dynamic beam-off thresholds is described below in conjunction with FIG. 10.

Figure 9:
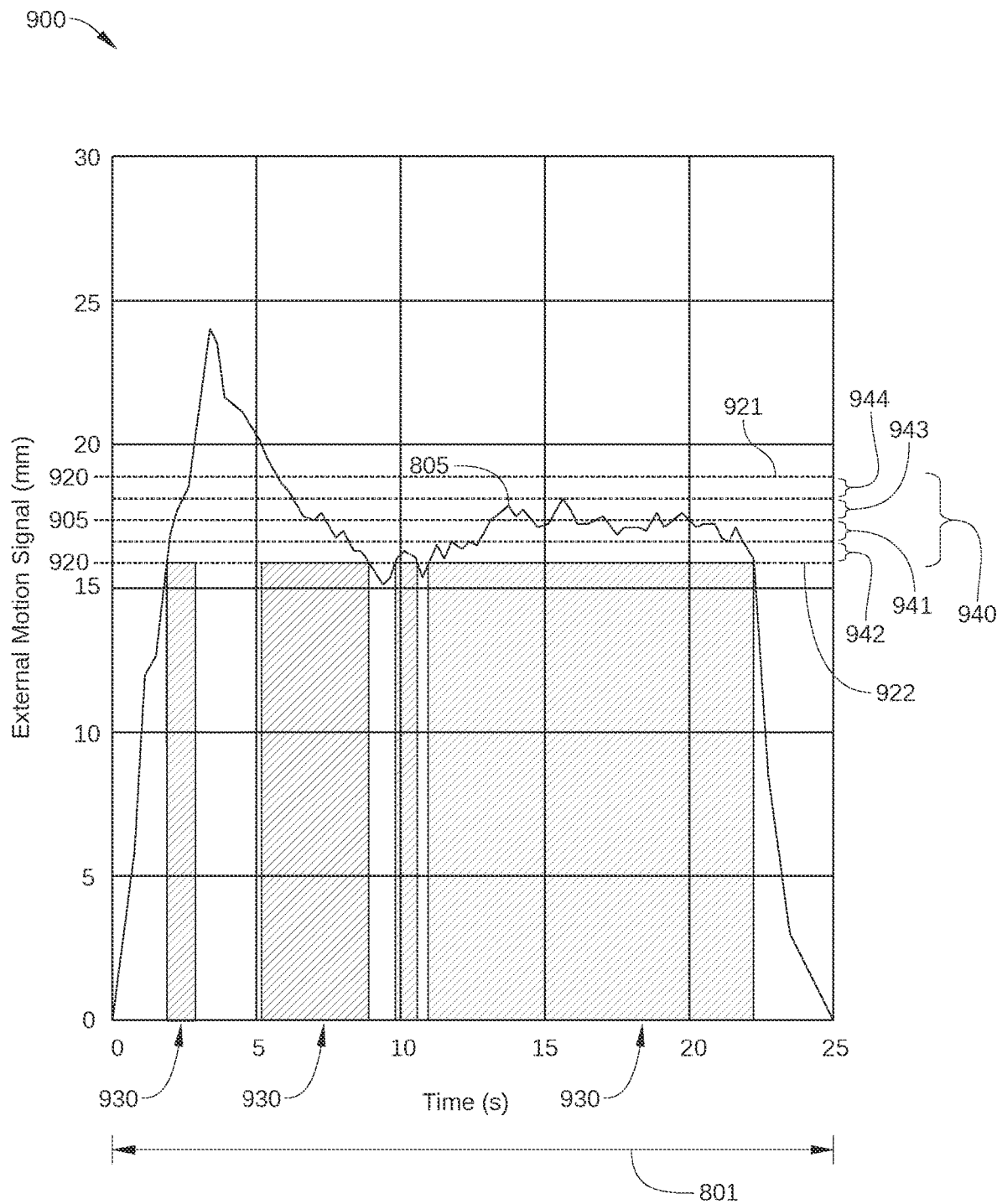
FIG. 9 is an illustration of a breath-hold correlation curve with static beam-off thresholds, according to various embodiments.

FIG. 9 is an illustration of a breath-hold correlation curve 900 with static beam-off thresholds 920, according to various embodiments. Breath-hold correlation curve 900 is substantially similar to breath-hold correlation curve 800 of FIG. 8, and shows target position 805 over time interval 801. As described above, in some embodiments target position 805 is not measured directly, and instead is determined by a computing device based on an external motion signal that is correlated to target position 805. In addition, FIG. 9 shows static beam-off thresholds 920 and an ideal target position 905.

Ideal target position 905 indicates a desired position of a target (e.g., a target volume, a position of a specific portion of a target volume, a position of an OAR, a position of a specific portion of an OAR, etc.) during breath-hold-based radiation treatment of a patient. In some embodiments, ideal target position 905 corresponds to the location of the target when the patient correctly performs a breath hold at the treatment breath-hold level for the patient. Thus, ideal target position 905 corresponds to the breath-hold level that is determined to be the breath-hold level that corresponds to the best-performing 3D model generated in step 602.

Static beam-off threshold 920 indicates allowable movement of a target during breath-hold-based radiation treatment of the patient, where the allowable movement does not violate one or more dosimetric or geometric parameters of the treatment planning directive. Thus, when target position 805 is greater than an upper static beam-off threshold 921 or less than a lower static beam-off threshold 922 during radiation treatment, a beam-hold occurs and the treatment beam is shut off.

FIG. 9 also shows beam-on times 930 (cross-hatched) that occur during time interval 801. As shown, beam-on times 930 occur during time interval 801 when target position 805 is within a range of beam-off threshold positions for the target region. Thus, in the embodiment illustrated in FIG. 9, beam-on times 930 occur when target position 805 is less than upper static beam-off threshold 921 and greater than lower static beam-off threshold 922.

In some embodiments, to avoid frequent beam-holds, beam-on times 930 continue for a predetermined time interval after target position 805 is determined to be greater than upper static beam-off threshold 921 or less than lower static beam-off threshold 922. In such embodiments, the predetermined time interval is generally short, for example less than one second, and can be a user-defined value, a system-defined value, or a value based on dosimetric analysis of the current breath-hold-based portion of a treatment fraction.

In some embodiments, breath-hold correlation curve 900 includes multiple dose bins 940 that are adjacent or proximate to ideal target position 905. In such embodiments, each dose bin corresponds to a range of target positions associated with a particular breath-hold level. Thus, in the embodiment illustrated in FIG. 9, a dose bin 941 corresponds to target positions associated with a slightly lower breath-hold level than that associated with ideal target position 905, a dose bin 942 corresponds to target positions associated with a slightly lower breath-hold level than that associated with dose bin 941, a dose bin 943 corresponds to target positions associated with a higher breath-hold level than that associated with ideal target position 905, and a dose bin 944 corresponds to target positions associated with a slightly higher breath-hold level than that associated with dose bin 943.

Dose bins 940 enable more accurate determination of dosing of non-target tissue during beam-on times 930. Further, in some embodiments, dose bins enable determination of dosing of specific regions of non-target tissue during beam-on times 930. For example, in some embodiments, non-target tissue that receives higher dosing when target position 805 is disposed within dose bin 944 may differ from non-target tissue that receives higher dosing when target position 805 is disposed within dose bin 942. Thus, dose bins 940 enable more granular determination of dosing of non-target tissue during a breath-hold-based portion of a treatment fraction.

In the embodiment illustrated in FIG. 9, breath-hold correlation curve 900 includes four dose bins 941-944, but in other embodiments, breath-hold correlation curve 900 can include more than or fewer than four dose bins 940. Further, in the embodiment illustrated in FIG. 9, dose bins 940 are symmetric in size and position relative to ideal target position 905, but in other embodiments, dose bins 940 may each represent different-sized ranges of target position 805.

Figure 10:
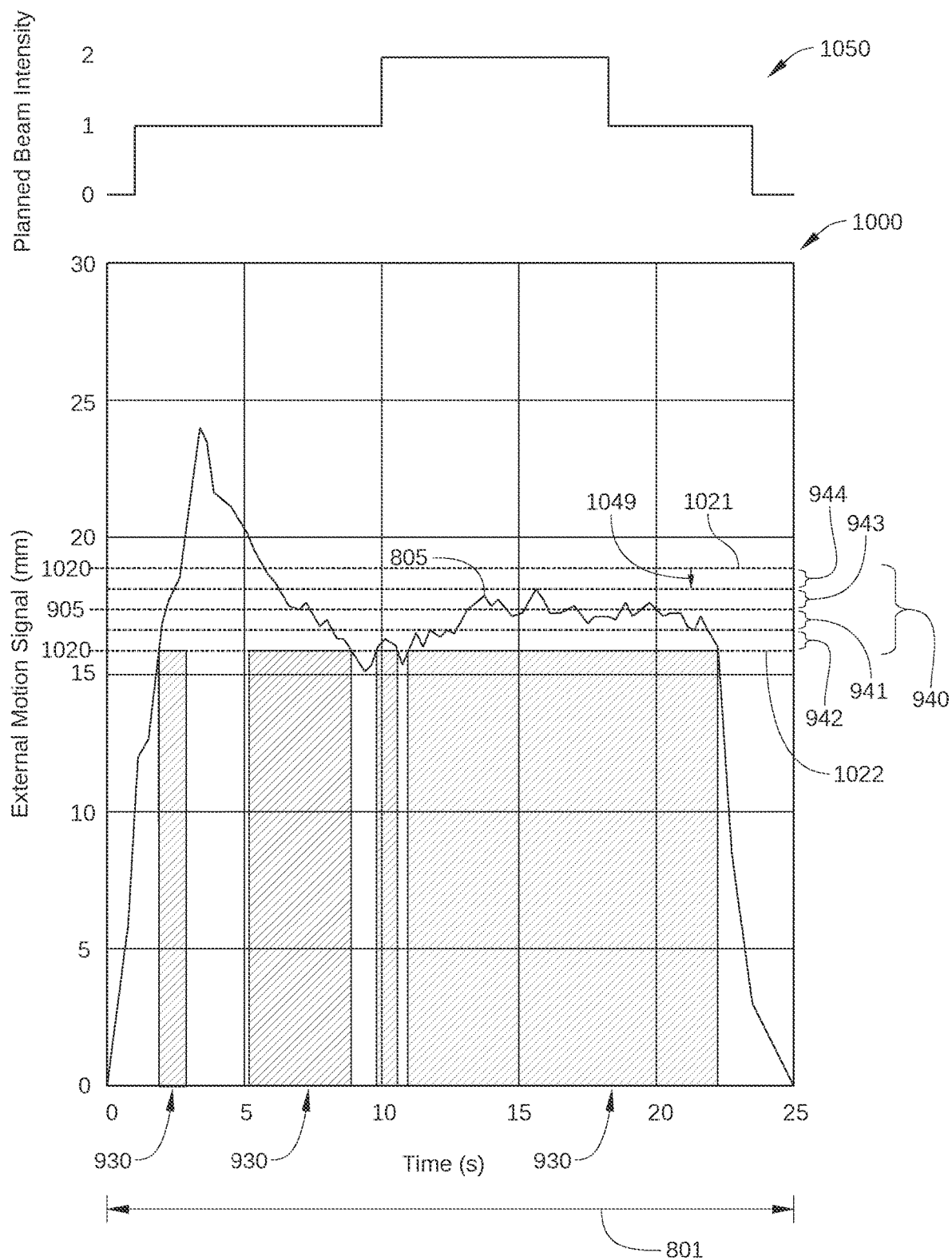
FIG. 10 is an illustration of a breath-hold correlation curve with dynamic beam-off thresholds, according to various embodiments.

FIG. 10 is an illustration of a breath-hold correlation curve 1000 with dynamic beam-off thresholds 1020, according to various embodiments. Breath-hold correlation curve 1000 is substantially similar to breath-hold correlation curve 900 of FIG. 9, and shows target position 805 over time interval 801, ideal target position 905, and dose bins 940. In addition, FIG. 10 shows dynamic beam-off thresholds 1020.

Dynamic beam-off thresholds 1020 enable dose monitoring during radiation treatment that is based on which specific dose bin target position 805 is located in and on the time during which target position 805 remains within that specific dose bin. The monitored dosing of non-target tissue proximate the target is then compared to a dose budget for such non-target tissue to determine whether a position of one or both dynamic beam-off thresholds 1020 should be modified. In some embodiments, based on the remaining dose budget and on the accumulated dose associated with the current target position 805, a dynamic beam-off threshold 1020 may be modified. For example, when a dosing of non-target tissue associated with dose bin 944 is determined to have exceeded (or alternatively is predicted to exceed) a dose budget for the non-target tissue, dynamic beam-off threshold 1021 is moved from a boundary of dose bin 944 to a boundary of dose bin 943, as indicated by arrow 1049. Thus, in such embodiments, a dynamic beam-off threshold 1020 is modified by associating the position of the dynamic beam-off threshold 1020 with a first range of target positions (e.g., the target positions represented by dose bin 943) and dissociating the position of the dynamic beam-off threshold 1020 from a second range of target positions (e.g., the target positions represented by dose bin 944).

In some embodiments, monitoring the dosing of non-target tissue is based on the dose bin 940 in which current target position 805 is disposed and on a current beam (or beamlet) intensity. Thus, in such embodiments, during a specific time interval, the dosing of non-target tissue is a function of the duration of the specific time interval, the planned beam intensity, and the particular dose bin in which current target position 805 is disposed. By way of example, FIG. 10 includes a beam intensity plot 1050 showing the different levels of beam intensity planned to occur during time interval 801.

Returning to FIG. 6, in step 608, the computing device determines whether the (static or dynamic) beam-off thresholds meet physician intent and/or other goals included in the treatment planning directive. For example, in some embodiments, the computing device determines whether a particular beam-off threshold meets goals included in the treatment planning directive by simulating application of the treatment plan associated with the best-performing 3D model generated in step 605 while the target position 805 is at that particular beam-off threshold. When such simulation indicates that the particular beam-off threshold fails to meet one or more goals included in the treatment planning directive, and the particular beam-off threshold is based on a breath-hold level that is adjacent to the treatment breath-hold level, there is little or no beam-off threshold available. Consequently, use of the treatment breath-hold level and the associated treatment plan will generally result in frequent beam holds. In such an instance, the goals of the treatment planning directive and patient anatomy are not compatible, and modification of the treatment planning directive is requested. Thus, when the computing device determines in step 608 that one or more beam-off thresholds fail to meet one or more goals included in the treatment planning directive, dosimetric analysis phase 502 proceeds to step 611; when the computing device determines the beam-off thresholds meet all goals included in the treatment planning directive, dosimetric analysis phase 502 proceeds to step 613.

In step 611, the computing device requests one or more modifications to the treatment planning directive and/or generates a notification/warning that the treatment planning directive requires modification.

In step 612, the computing device receives a modified treatment planning directive. In some instances, the treatment planning directive is modified by a physician and in other instance by treatment planning software. In some instances, the modified treatment planning directive includes modified dose volume and/or geometric parameters that facilitate non-zero beam-off thresholds for the anatomical structures and target volume location of the current patient. In some instances, the modified treatment planning directive includes an escalated tumor dose and/or geometric parameters that result in a tighter dose parameter.

In step 613, the computing device determines whether the beam-off thresholds determined in step 607 are too large. For example, in some embodiments, such a determination is made based on an absolute maximum threshold value (e.g., 5 mm), a maximum threshold value relative to a dose volume and/or geometric parameter included in the treatment planning directive, and/or a value based on a dosimetric analysis of the current breath-hold-based portion of a treatment fraction. When the computing device determines that one or more beam-off thresholds are too large, dosimetric analysis phase 502 proceeds to step 611; when the computing device determines that none of the beam-off thresholds are too large, dosimetric analysis phase 502 proceeds to step 620.

In step 620, the computing device finalizes the treatment plan associated with the best-performing 3D model generated in step 605.

Figure 11:
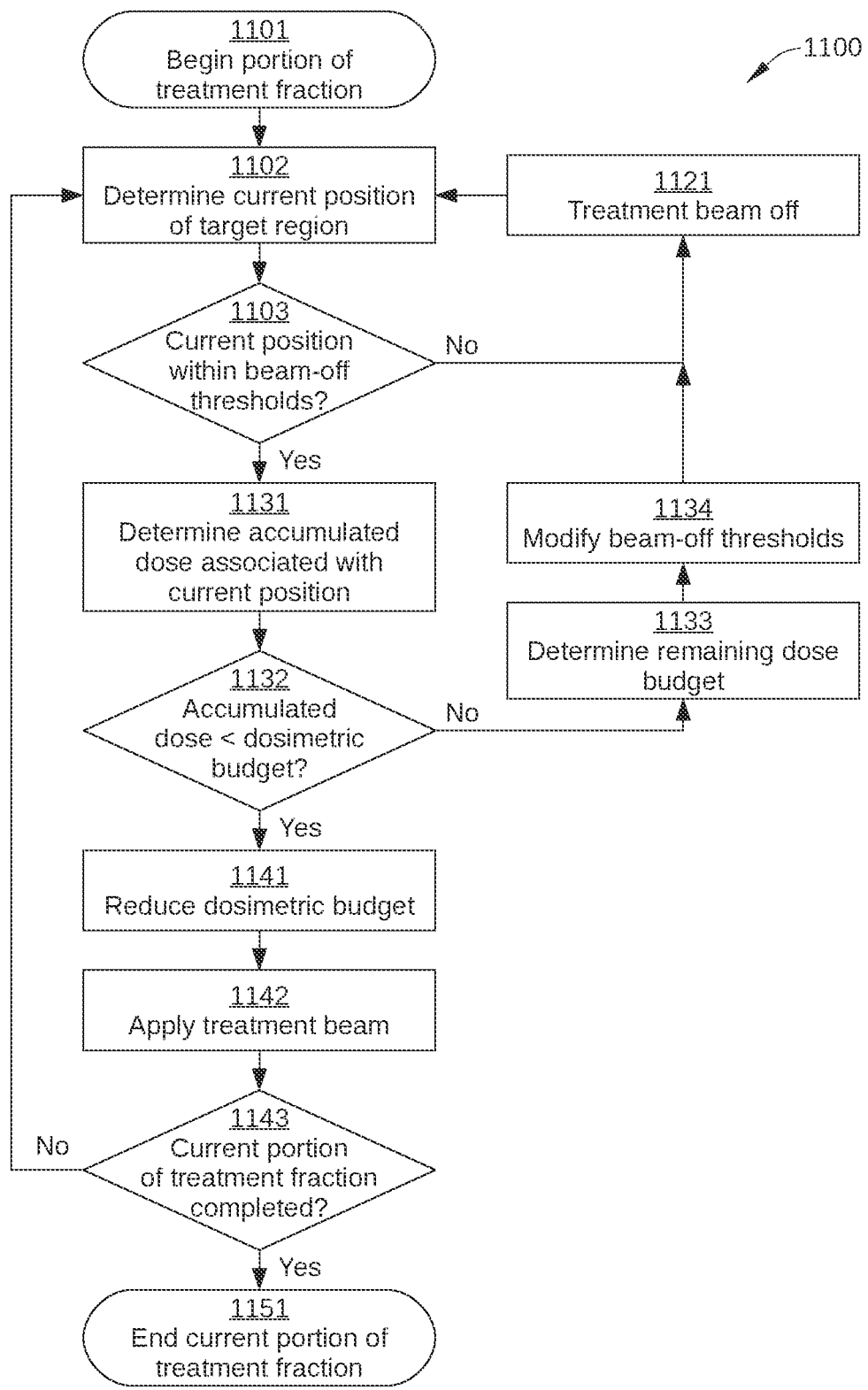
FIG. 11 sets forth a flowchart of a treatment fraction process of the radiation therapy phase of FIG. 5, according to one or more embodiments.

FIG. 11 sets forth a flowchart of a treatment fraction process 1100 of radiation therapy phase 503, according to one or more embodiments. As noted above, radiation therapy phase 503 generally includes multiple treatment fractions, each of which may include a single or multiple breath-hold-based portions that each occur over a single breath hold. In treatment fraction process 1100, a portion of the treatment plan generated in dosimetric analysis phase 502 is implemented in conjunction with static beam-off thresholds or dynamic beam-off thresholds. In some embodiments, treatment fraction process 1100 is performed over a single rotational arc of a gantry of radiation therapy system. Alternatively, in some embodiments, treatment fraction process 1100 is performed over multiple rotational arcs of a gantry of a radiation therapy system. Alternatively, in some embodiments, treatment fraction process 1100 is performed over a fraction of a rotational arc of a gantry of a radiation therapy system or over multiple separate fractions of a rotational arc of the gantry. Alternatively, in some embodiments, treatment fraction process 1100 is performed in a static-gantry radiation therapy process, such as an IMRT or a 3D conformal radiation therapy process. Treatment fraction process 1100 may include one or more operations, functions, or actions as illustrated by one or more of blocks 1101-1151. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although treatment fraction process 1100 is described in conjunction with the systems of FIGS. 1-10, persons skilled in the art will understand that any suitably configured radiation therapy system is within the scope of the present embodiments.

In step 1101, a radiation therapy system begins implementation of the current breath-hold-based portion of a treatment fraction. In step 1102, the radiation therapy system determines the current target position 805. In some embodiments, current target position 805 is determined based on an external motion signal. Additionally, in some embodiments, the determination of current target position 805 is further based on 3D imaging of the anatomical region surrounding a target volume of the patient. In such embodiments, the 3D imaging (e.g., a 3D CT scan) is employed to periodically correct the target position 805 indicated by the external motion signal.

In step 1103, the radiation therapy system determines whether the current target position 805 is within the beam-off thresholds generated for treatment fraction process 1100. If yes, treatment fraction process 1100 proceeds to step 1131; if no, treatment fraction process 1100 proceeds to step 1121. In step 1121, radiation therapy system performs a beam hold and shuts off the one or more treatment beams to be applied to the target volume for a predetermined time interval. Alternatively, in some embodiments, compensatory couch motion is employed to prevent target position 805 from moving outside the beam-off thresholds and thereby avoid a beam hold.

In step 1131, the radiation therapy system determines an accumulated dose that will occur if a treatment beam is applied to the target volume based on the current target position 805. As noted above, the accumulated dose may be based on the particular dose bin in which current target position 805 is disposed, the duration of the time interval during which the treatment beam is applied while target position 805 is disposed within the particular dose bin, and/or the beam intensity of the treatment beam while target position 805 is disposed within the particular dose bin.

In step 1132, the radiation therapy system determines whether the accumulated dose determined in step 1131 is less than a current dose budget. In some embodiments, the dose budget is associated with all non-target tissue proximate the target volume. In other embodiments, the dose budget is associated with a specific anatomical structure and/or other critical structure or tissue type that is proximate the target volume. When the radiation therapy system determines that the accumulated dose determined in step 1131 is less than the current dose budget, treatment fraction process 1100 proceeds to step 1141; when the radiation therapy system determines that the accumulated dose determined in step 1131 is greater than the current dose budget, treatment fraction process 1100 proceeds to step 1133.

In step 1133, the radiation therapy system determines a remaining dose budget for non-target tissue, where the remaining dose budget is less than the current dose budget. According to various embodiments, a lower dose budget generally results in stricter beam-off thresholds, as described below. In general, a lower dose budget (such as the remaining dose budget determined in step 1133) results in stricter beam-off thresholds because a treatment beam can no longer be safely applied while target position 805 is located in dose bins that are farther from ideal target position 905.

In step 1134, the radiation therapy system modifies one or more beam-off thresholds based on the remaining dose budget determined in step 1133. For example, in some embodiments, dynamic beam-off threshold 1021 is moved from a boundary of one dose bin (e.g., dose bin 944) to a boundary of a different dose bin that is closer to ideal target position 905 (e.g., dose bin 943) in response to the remaining dose budget determined in step 1133.

In step 1141, the radiation therapy system reduces the accumulated budget by the accumulated dose determined in step 1131. In step 1142, the radiation therapy system applies the treatment beam or beams to the target volume for a predetermined time interval, for example until a new target position 805 can be determined.

In step 1143, the radiation therapy system determines whether the current breath-hold-based portion of a treatment fraction has been completed. If no, treatment fraction process 1100 returns to step 1102, and radiation therapy system continues the treatment fraction; if yes, treatment fraction process 1100 proceeds to step 1151, and radiation therapy system ends the current breath-hold-based portion of a treatment fraction. Treatment fraction process 1100 can then be employed to implement a subsequent breath-hold-based portion of the treatment fraction.

Treatment fraction process 1100 can be advantageously employed in stereotactic and/or hypofractionation treatments, in which relatively few treatment fractions (e.g., five or ten) are performed and excursions of target position 805 can have more serious effects. However, any other technically feasible radiation therapy process can benefit from the embodiments described herein, including techniques that include larger numbers of fractions (e.g., 20 or more).

In the embodiment of treatment fraction process 1100 described above, operations are performed with respect to a single dose budget, such as, for example, a dose budget associated with all non-target tissue proximate the target volume. In other embodiments, treatment fraction process 1100 can be performed with respect to multiple dose budgets. For example, in one such embodiment, a different dose budget is associated with and tracked for each different dose bin 940 of a breath-hold correlation curve employed in treatment fraction process 1100. Thus, in such an embodiment, in step 1131 the radiation therapy system may determine the accumulated dose for the current dose bin 940 in which target position 806 is located, and in step 1131 the radiation therapy system may determine whether the accumulated dose determined in step 1131 is less than a current dose budget for the current dose bin 940. As a result, in such embodiments, the multiple dose budgets are tracked separately for each does bin 940.

Figure 12:
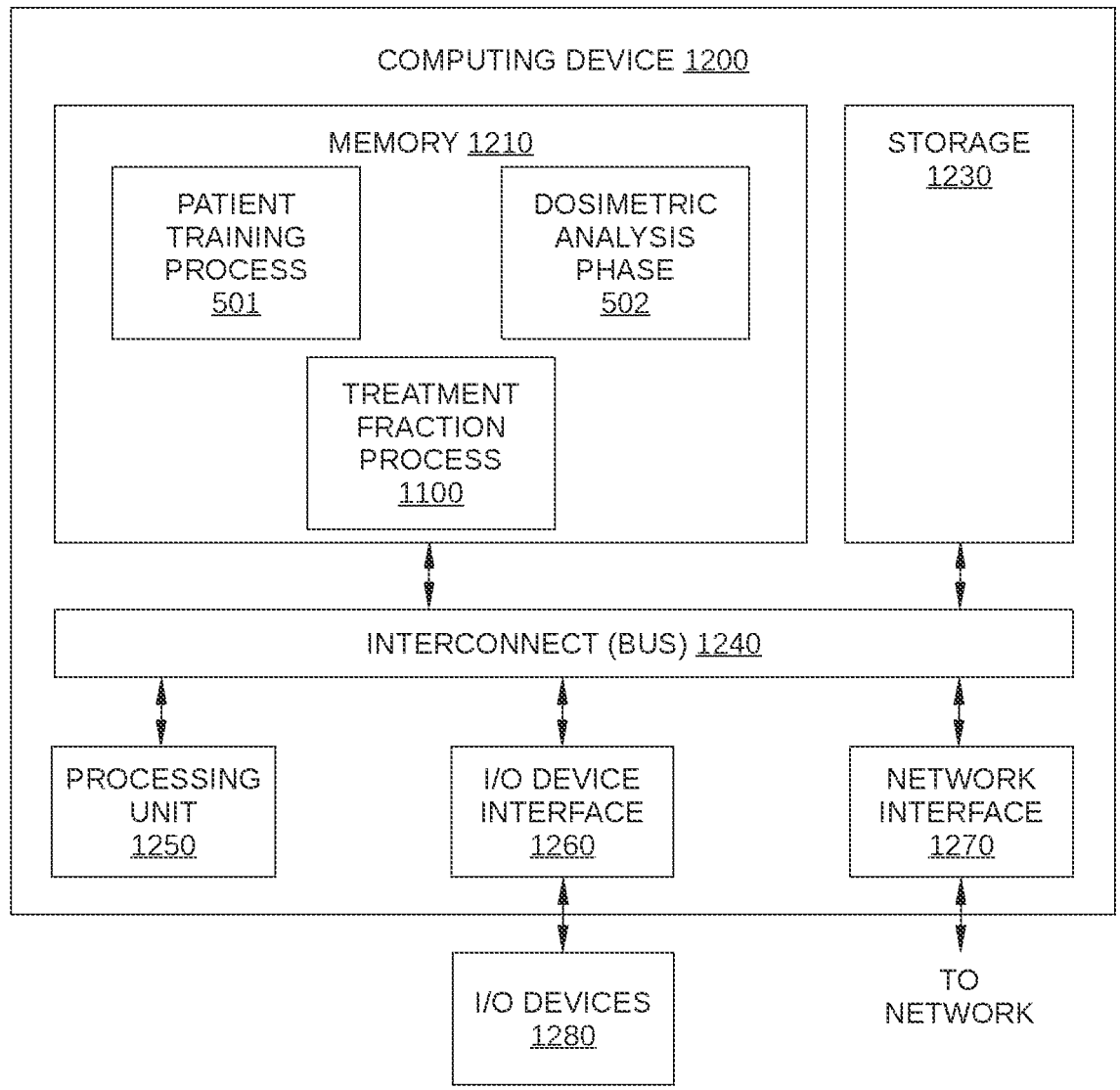
FIG. 12 is an illustration of a computing device configured to perform various embodiments of the present disclosure.

FIG. 12 is an illustration of computing device 1200 configured to perform various embodiments of the present disclosure. Computing device 1200 may be a desktop computer, a laptop computer, a smart phone, or any other type of computing device suitable for practicing one or more embodiments of the present disclosure. In operation, computing device 1200 is configured to execute instructions associated with patient training phase 501, dosimetric analysis phase 502, and/or treatment fraction process 1100 as described herein. It is noted that the computing device described herein is illustrative and that any other technically feasible configurations fall within the scope of the present disclosure.

As shown, computing device 1200 includes, without limitation, an interconnect (bus) 1240 that connects a processing unit 1250, an input/output (I/O) device interface 1260 coupled to input/output (I/O) devices 1280, memory 1210, a storage 1230, and a network interface 1270. Processing unit 1250 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 1250 may be any technically feasible hardware unit capable of processing data and/or executing software applications, including patient training phase 501, dosimetric analysis phase 502, and/or treatment fraction process 1100.

I/O devices 1280 may include devices capable of providing input, such as a keyboard, a mouse, a touch-sensitive screen, and so forth, as well as devices capable of providing output, such as a display device and the like. Additionally, I/O devices 1280 may include devices capable of both receiving input and providing output, such as a touchscreen, a universal serial bus (USB) port, and so forth. I/O devices 1280 may be configured to receive various types of input from an end-user of computing device 1200, and to also provide various types of output to the end-user of computing device 1200, such as displayed digital images or digital videos. In some embodiments, one or more of I/O devices 1280 are configured to couple computing device 1200 to a network.

Memory 1210 may include a random access memory (RAM) module, a flash memory unit, or any other type of memory unit or combination thereof. Processing unit 1250, I/O device interface 1260, and network interface 1270 are configured to read data from and write data to memory 1210. Memory 1210 includes various software programs that can be executed by processor 1250 and application data associated with said software programs, including patient training phase 501, dosimetric analysis phase 502, and/or treatment fraction process 1100.

Figure 13:
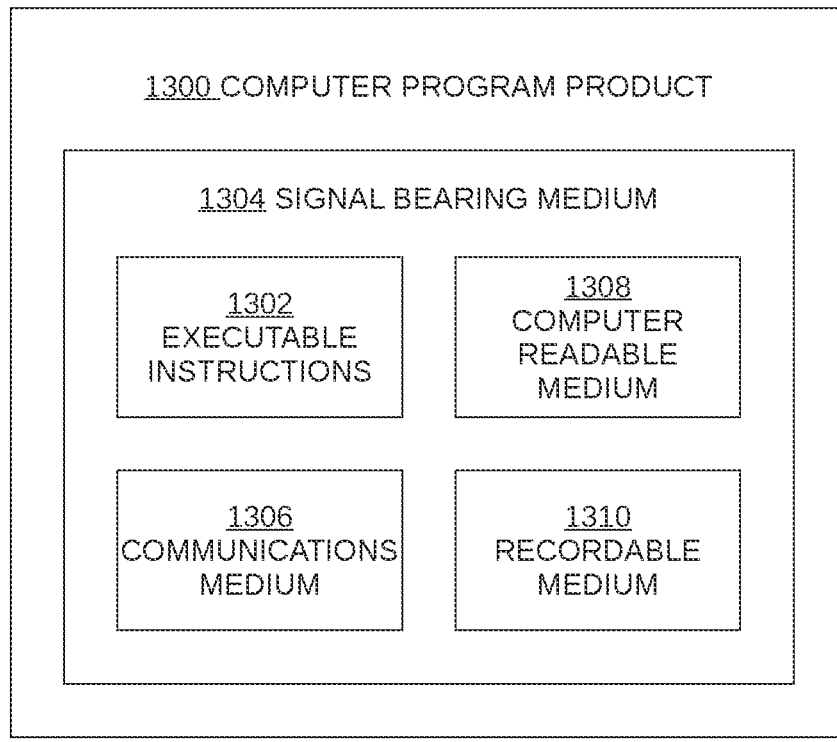
FIG. 13 is a block diagram of an illustrative embodiment of a computer program product for implementing one or more embodiments of the present disclosure.

FIG. 13 is a block diagram of an illustrative embodiment of a computer program product 1300 for implementing a method for segmenting an image, according to one or more embodiments of the present disclosure. Computer program product 1300 may include a signal bearing medium 1304. Signal bearing medium 1304 may include one or more sets of executable instructions 1302 that, when executed by, for example, a processor of a computing device, may provide at least the functionality described above with respect to FIGS. 1-12.

In some implementations, signal bearing medium 1304 may encompass a non-transitory computer readable medium 1308, such as, but not limited to, a hard disk drive, a Compact Disc (CD), a Digital Video Disk (DVD), a digital tape, memory, etc. In some implementations, signal bearing medium 1304 may encompass a recordable medium 1310, such as, but not limited to, memory, read/write (R/W) CDs, R/W DVDs, etc. In some implementations, signal bearing medium 1304 may encompass a communications medium 1306, such as, but not limited to, a digital and/or an analog communication medium (e.g., a fiber optic cable, a waveguide, a wired communications link, a wireless communication link, etc.). Computer program product 1300 may be recorded on non-transitory computer readable medium 1308 or another similar recordable medium 1310.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A computer-implemented method of performing a treatment fraction of radiation therapy, the method comprising:
   determining a current position of a target volume of patient anatomy;
   based on the current position of the target volume, computing an accumulated dose for tissue disposed within the target volume;
   determining that the accumulated dose is less than a current dose budget of the tissue; and
   in response to the accumulated dose being less than the current dose budget, applying a treatment beam to the target volume while the target volume is in the current position.

2. The computer-implemented method of claim 1, wherein the current position is at least partially outside a planned treatment location for the target volume.

3. The computer-implemented method of claim 1, further comprising generating a new value for the dose budget by subtracting the accumulated dose from the current dose budget.

4. The computer-implemented method of claim 3, further comprising, based on the new value of the dose budget, modifying a beam-off threshold position for the target volume.

5. The computer-implemented method of claim 4, wherein modifying the beam-off threshold position for the target volume comprises associating the beam-off threshold position with a first range of target positions and disassociating the beam-off threshold position from a second range of target positions, wherein the first range of target positions is closer to a planned treatment location for the target volume than the second range of target positions.

6. The computer-implemented method of claim 1, further comprising, prior to applying the treatment beam to the target volume, determining that the current position is within a range of beam-off threshold positions for the target volume.

7. The computer-implemented method of claim 6, further comprising, when a detected position of the target volume is outside the range of beam-off threshold positions, blocking application of the treatment beam for a portion of the treatment fraction.

8. The computer-implemented method of claim 1, further comprising:
   determining an equivalent breath-hold level based on the current position of the target volume; and
   computing the accumulated dose based on the equivalent breath-hold level.

9. The computer-implemented method of claim 8, wherein the equivalent breath-hold level is associated with a specific accumulated dose.

10. The computer-implemented method of claim 1, further comprising:
    determining a treatment beam intensity that is applied to the target volume while the target volume is in the current position; and
    computing the accumulated dose based on the treatment beam intensity.

11. The computer-implemented method of claim 1, wherein determining the current position of the target volume comprises measuring an external motion signal.

12. The computer-implemented method of claim 1, wherein determining the current position of the target volume further comprises performing X-ray imaging of the target volume.

13. The computer-implemented method of claim 1, further comprising based on the current position of the target volume, computing an accumulated dose for the tissue.

14. A system for performing a treatment fraction of radiation therapy, the system comprising:
an X-ray imaging device;
a treatment-delivering X-ray source configured to direct treatment X-rays to a target volume of patient anatomy;
an imaging X-ray source configured to direct imaging X-rays through the target volume and toward the X-ray imager; and
a processor configured to:
determine a current position of the target volume;
based on the current position of the target volume, compute an accumulated dose for tissue disposed within the target volume;
determine that the accumulated dose is less than a current dose budget of the tissue; and
in response to the accumulated dose being less than the current dose budget, cause the treatment-delivering X-ray source to apply a treatment beam to the target volume while the target volume is in the current position.

15. The system of claim 14, wherein the current position is at least partially outside a planned treatment location for the target volume.

16. The system of claim 14, wherein determining the current position of the target volume further comprises performing X-ray imaging of the target volume with the X-ray imaging device and the imaging X-ray source.

17. The system of claim 14, wherein causing the treatment-delivering X-ray source to apply the treatment beam to the target volume while the target volume is in the current position comprises a portion of the treatment fraction.

18. A computer-implemented method of performing a treatment fraction of radiation therapy, the method comprising:
determining a current position of a target volume of patient anatomy;
based on the current position of the target volume, computing an accumulated dose for tissue associated with the target volume;
determining that the accumulated dose is greater than a current dose budget of the tissue; and
in response to the accumulated dose being greater than the current dose budget:
determining a remaining dose budget for the tissue associated with the target volume; and
based on the remaining dose budget for the tissue, modifying a beam-off threshold position for the target volume.

19. The computer-implemented method of claim 18, wherein the tissue associated with the target volume comprises one of tissue disposed within the target volume or non-target tissue proximate the target volume.

20. The computer-implemented method of claim 19, further comprising:
determining a new position of the target volume;
based on the new position of the target volume, computing a new accumulated dose for the tissue;
determining that the new accumulated dose is less than the remaining dose budget for the tissue; and
in response to the accumulated dose being less than the current dose budget, applying a treatment beam to the target volume while the target volume is in the new position.

* * * * *